(12) United States Patent
Dang et al.

(10) Patent No.: US 10,849,516 B2
(45) Date of Patent: Dec. 1, 2020

(54) INTELLIGENT HEALTH STRAP

(71) Applicant: ARNUXON PHARM-SCI CO., LTD., Beijing (CN)

(72) Inventors: Zhijing Dang, Beijing (CN); Guangteng Wu, Beijing (CN); Liankai Dang, Beijing (CN)

(73) Assignee: ARNUXON PHARM-SCI CO., LTD., Beijing (CN)

( * ) Notice: Subject to any disclaimer, the term of this patent is extended or adjusted under 35 U.S.C. 154(b) by 480 days.

(21) Appl. No.: 15/513,879

(22) PCT Filed: Dec. 24, 2015

(86) PCT No.: PCT/CN2015/000928
§ 371 (c)(1),
(2) Date: Jul. 17, 2017

(87) PCT Pub. No.: WO2016/106768
PCT Pub. Date: Jul. 7, 2016

(65) Prior Publication Data
US 2017/0354336 A1    Dec. 14, 2017

(30) Foreign Application Priority Data

Dec. 30, 2014 (CN) .......................... 2014 1 0833765
Jul. 15, 2015 (CN) .......................... 2015 1 0416950

(51) Int. Cl.
*A61B 5/024* (2006.01)
*A61B 5/00* (2006.01)
(Continued)

(52) U.S. Cl.
CPC ........ *A61B 5/02438* (2013.01); *A61B 5/0404* (2013.01); *A61B 5/681* (2013.01);
(Continued)

(58) Field of Classification Search
CPC ............ A61B 5/14552; A61B 5/02438; A61B 5/04085; A61B 5/681; A61B 5/024; A61B 5/02405–02433; A61H 39/04
See application file for complete search history.

(56) References Cited

U.S. PATENT DOCUMENTS 3,364,922 A * 1/1968 Akihiko ............. A61H 23/0263
601/72
2006/0229519 A1* 10/2006 Fujiwara ............ A61B 5/02007
600/500
(Continued)

FOREIGN PATENT DOCUMENTS

| CN | 101617940 | 1/2010 |
|---|---|---|
| CN | 102144916 | 8/2011 |

(Continued)

OTHER PUBLICATIONS

International Search Report of International Application No. PCT/CN2015/000928 dated Mar. 21, 2016.

*Primary Examiner* — Devin B Henson
*Assistant Examiner* — H. Q. Nguyen
(74) *Attorney, Agent, or Firm* — Ping Wang; Morris, Manning & Martin LLP

(57) ABSTRACT

An intelligent health strap. A detection and analysis method comprises: acquiring multiple groups of pulse data collected by multiple pulse sensors (11); and according to the multiple groups of pulse data, using a calculation method for analysis to obtain physical sign information (12). An intelligent health wrist strap and an intelligent health ankle strap having multiple pulse sensors are used for performing pulse monitoring and analysis, displaying multiple types of pulse physical sign information, and transmitting data to an external device, so that a user can conveniently monitor changes of individual physiological status, and the intelligent health wrist strap and the intelligent health ankle strap can provide massage and health-care for wrists and ankles.

9 Claims, 2 Drawing Sheets

(51) Int. Cl.
  *A61H 39/04* (2006.01)
  *A61B 5/0404* (2006.01)
  *A61B 5/0245* (2006.01)

(52) U.S. Cl.
  CPC ............ *A61H 39/04* (2013.01); *A61B 5/0245* (2013.01); *A61B 2562/04* (2013.01); *A61H 2201/1215* (2013.01); *A61H 2201/165* (2013.01); *A61H 2201/1635* (2013.01); *A61H 2201/1671* (2013.01); *A61H 2201/501* (2013.01); *A61H 2201/5012* (2013.01); *A61H 2201/5025* (2013.01); *A61H 2201/5043* (2013.01); *A61H 2201/5058* (2013.01); *A61H 2205/065* (2013.01); *A61H 2230/06* (2013.01); *A61H 2230/202* (2013.01); *A61H 2230/30* (2013.01); *A61H 2230/42* (2013.01)

(56) References Cited

U.S. PATENT DOCUMENTS

| | | | | |
|---|---|---|---|---|
| 2010/0056934 A1* | 3/2010 | Cho | ............... | A61B 5/02416 600/502 |
| 2011/0009713 A1* | 1/2011 | Feinberg | ............... | A61B 5/0205 600/301 |
| 2012/0184829 A1* | 7/2012 | Sekii | ............... | A61B 5/021 600/323 |
| 2014/0350441 A1* | 11/2014 | Shafieloo | ............... | A61H 23/0263 601/48 |
| 2015/0265217 A1* | 9/2015 | Penders | ............... | A61B 5/721 600/301 |
| 2015/0287338 A1* | 10/2015 | Wells | ............... | G09B 19/0038 702/19 |
| 2016/0070393 A1* | 3/2016 | Sharma | ............... | G06F 1/163 345/174 |

FOREIGN PATENT DOCUMENTS

| | | |
|---|---|---|
| CN | 102327114 | 1/2012 |
| CN | 202489940 | 10/2012 |
| CN | 203953630 | 11/2014 |
| CN | 104799835 | 7/2015 |
| CN | 204542080 | 8/2015 |
| CN | 204744129 | 11/2015 |
| CN | 105105727 | 12/2015 |
| EP | 1 757 225 | 2/2007 |
| JP | 62176429 | 8/1987 |
| WO | 8200950 | 4/1982 |

\* cited by examiner

INTELLIGENT HEALTH STRAP

This application is a national stage application of International Patent Application No. PCT/CN2015/000928, filed Dec. 24, 2015, which claims priority to China patent Application Nos. 201410833765.3, filed Dec. 30, 2014 and 201510416950.7, filed Jul. 15, 2015. The entirety of the aforementioned applications is incorporated herein by reference.

FIELD

The present invention is directed to an apparatus for health monitor and health care, especially as an intelligent health band.

BACKGROUND

As the development of science and technology, more and more personal wearable health monitor products have been made, which have many functions including step count, pulse measurement, calorie measurement, sleep monitor, physical-training options, incoming call alert, Bluetooth communication, etc.; and the wearable products are designed as bracelet, watch and so on.

Some examples of the main brand products are: (1) Huawei bracelets, doing near-field communication (NFC), step count, sleep monitor, waterproof IP57, incoming call alert and long-time sitting alert, etc.; (2) Samsung Gear Fit R350, doing pulse measurement, acceleration sensor detection, Bluetooth, etc.; (3) Garmin Vivofit, doing step count, calorie measurement, pulse measurement, sleep monitor, Bluetooth, etc.; (4) Jawbone UP24, doing intelligent alarm-clock, sleep monitor, step count, physical training options, etc.; (5) Razer Nabu, doing step count, sleep monitor, accelerometer, vibrator, Bluetooth, etc.

The above mentioned functions of the example products are useful, but these functions are more in the fields of movement monitoring and Bluetooth communication, and simple in personal health monitoring. The present available personal health monitor products usually have a single function, for instance, sphygmomanometer, thermometer and oximeter. The medicine equipment, for instance, ECG (electrocardiogram) monitor, having 12 or 18-leads to place at different points on body to detect a group of signals, are usually big in size, and complicated for general people to follow the operational procedures, which are not designed for general people to carry and use at any time. Besides, the present personal wristband products have several disadvantages, including improper sensor positions, and the limited number and types of sensors. For example, when using infrared sensor of 940 nm wavelength to detect blood oxygen or within 1000 nm for other physical signal detection, big signal floating or other reasons may lead to improper or wrong analysis of physiological conditions, including blood pressure, blood glucose level, artery stiffness, etc. Moreover, the important aspects of health care including both massage function and health monitor haven't been designed in one product yet. Therefore, an intelligent health band product having multi-functions to help improve user's health condition is strongly needed.

SUMMARY

Based on the above statements, the main purpose of present invention is to provide a method for health information detection and analysis, a health-monitor and massage device, and a terminal system. Specifically, the invention comprises: acquiring multiple groups of pulse signal data detected by a plurality of pulse sensors over wrist and ankle, analyzing the multiple groups of pulse signal data for physiological characteristics by employing mathematical methods, displaying the physical signal information on a display screen of wristband, transmitting data to a peripheral device through Bluetooth and other ways for users' convenience to check their health conditions; and massaging acupuncture points around the wrist and the ankle.

The invention of technical solutions adopted comprises:
providing a method of detecting and analyzing health information, the method includes the following steps:
acquiring multiple groups of pulse signal data detected by a plurality of pulse sensors;
analyzing the multiple groups of pulse signal data for physiological characteristics by employing mathematical methods.

In some further implementations of the method, the method for detection and analysis of health information includes the following steps:
sending the physical signal information to a display screen of a terminal device for display.

The invention provides a device for detection and analysis of health information, the device comprises:
a first acquisition module for acquiring multiple groups of pulse data detected by a plurality of pulse sensors; and
a first analysis module for obtaining physiological characteristics through analysis using calculation methods according to the pulse data.

The said device for detection and analysis of health information, characterized in that it further comprises a display control module for sending data to a display screen of a terminal for display.

Further, a terminal is provided, the terminal comprises the device for detection and analysis of health information, wherein the device for detection and analysis is the main control module of the terminal;
and the said main control module is mounted on a mainboard of the said terminal, the said main control module comprises connecting with two or more than two pulse sensors provided thereon.

The said mainboard of the said terminal comprises a storage module and a communication module in signal connection with the said main control module.

In some implementations of the device, an intelligent health band is provided, which comprises a wrist band and an ankle band, wherein both the wrist band and the ankle band comprise an electronic control module as well as two or more than two pulse sensors and one or more miniature massagers.

The said electronic control module comprises a main control module, as well as a storage module and a communication module in signal connection with the said main control module.

The said pulse sensor and the mini massager comprise mounting in the inner side of the band.

The said intelligent health band characterized in that, the said wrist band comprises a touch control display screen which is in signal connection with the main control module in the wrist band, controlling the state of the wrist band and communicating with the ankle band through a Bluetooth module so as to control the state of the ankle band.

In comparison with existing technology, this invention has the following advantages: (1) this invention comprises acquiring multiple groups of pulse signal data detected by two or more pulse sensors on the wristband and the ankle band, respectively, analyzing the multiple groups of pulse signal data and generating three dimensional pulse signal data to achieve physiological characteristics by employing mathematical methods, such as blood oxygen, heart rate, breathe rate, blood pressure, blood glucose, artery stiffness, etc., performing real-time health monitoring, and easy to carry and use; (2) further, the wristband and ankle band are equipped with mini massagers which can be adjusted to acupuncture points on the wrist and ankle, and massage at any time quietly while doing other activities; (3) furthermore, the stored detected pulse data can be displayed on a touch screen of the wristband, and transmitted to an external device through Bluetooth or other methods of communication for analyzing and presenting, so users have more ways to check their physiological conditions.

DETAILED DESCRIPTION

To illustrate the technical problems to be solved, technical solutions and the advantages of the invention, more details and embodiments are described with FIGS. 1-4.

Figure 1:
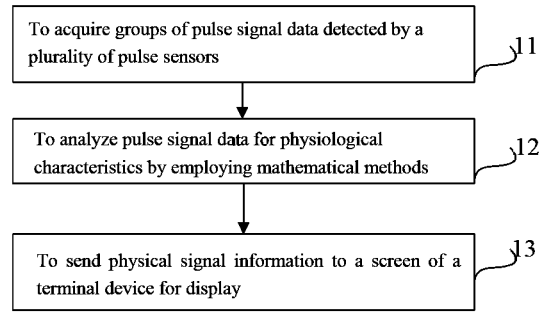
FIG. 1 is a flow diagram presenting steps of detection and analysis of health information.

As shown in FIG. 1, the invention of the method for detection and analysis of health information, characterized in that it comprises:

step 11 of acquiring multiple groups of pulse signal data detected by a plurality of pulse sensors;

step 12 of analyzing the multiple groups of pulse signal data for physiological characteristics by employing mathematical methods.

Further, the method for detection and analysis of health information, characterized in that it comprises the following step of:

step 13 of sending the physical signal information to a display screen of a terminal device for display.

This implementation of the method comprises: analyzing detected pulse data to get several items of physical conditions, and displaying the information on a screen of the wristband or other terminal equipment for users to check their health condition changes conveniently.

In an implementation of the method, step 11 of the method comprises: step 111 of acquiring intensity-time sequence data of the multiple groups of pulse data collected by a plurality of pulse sensors which are represented by $I_{1i} \sim t_{1i}$, $I_{2i} \sim t_{2i}$, ..., $I_{ni} \sim t_{ni}$, wherein I represents the intensity of pulse signals collected by pulse sensors, n represents a sensor number, $n \geq 1$, and i represents a time sequence number detected, $i=1, 2, 3 \ldots$.

According to step 111, the obtained multiple groups of intensity-time sequence data comprises five implementations:

in the implementation one, according to the following equation (1):

$$\Delta I_{ni-nj} = I_{ni} - I_{nj} \qquad (1)$$

obtaining a difference between effective intensities at an i-th time and a j-th time detected by a n-th sensor;

wherein i and j stand for time number, $j-i=1, 2, 3 \ldots$;

further, when $\Delta I_{ni-nj} - \Delta I_{ni-n(j+1)} \leq 0$, and $\Delta I_{ni-n(j+1)} \leq \Delta I_{ni-n(j+2)}$, and $\Delta I_{ni-n(j-1)} \geq \Delta I_{ni-nj}$, then the corresponding intensity difference of the n-th sensor from the i-th time to the j-th time is denoted as $\Delta IM_{ni-nj}$.

The implementation two comprises:
according to the following formulae (2):

$$\Delta I_{ni-mi} = I_{ni} - I_{mi} \qquad (2)$$

obtaining intensities differences collected by the n-th sensor and m-th sensor of the same type at the i-th time, wherein $m \neq n$ The implementation three comprises:
according to the following equation (3):

$$A_{ni-nj} = I_{ni} + I_{n(i+1)} + \ldots + I_{nj} \qquad (3)$$

obtaining a summation of signal intensities collected by a single sensor;

wherein A stands for the summation of intensity data, I stands for a signal intensity, n stands for the sensor number, and i and j stand for different time sequence numbers.

In further implementation, the method comprises the following step of:

according to the equation (4):

$$\mu_{nm/ij} = A_{ni-nj} / A_{mi-mj} \qquad (4)$$

obtaining the ratio between the sums of intensities detected by multiple sensors;

wherein $\mu_{nm/ij}$ represents the ratio between the sums of intensities within the same time period of i-j in respective pulse intensity curves detected by a m-th sensor and a n-th sensor.

The implementation four comprises:
When $I_{ni} > I_{n(i+1)}$ and $I_{ni} > I_{n(i-1)}$, according to the equation (5):

$$IM_{ni} = I_{ni} \qquad (5)$$

obtaining a series of pulse peak values $IM_{ni}$~time sequence i;

if in the series of peak values IM appears continuously in two adjacent peaks $IM_{ni}$ and $IM_{nj}$ at $h*(j-i)$, ($h=1, 2 \ldots$), a single pulse duration is $f=(j-i)*a$, wherein a is a constant of time duration between detected signals, $a=1/q$; and the pulse per minute is $60/f$;

wherein $h=1, 2, 3, \ldots$; i and j represent different time sequence numbers;

and q represents the number of detected signals per second.

The implementation five comprises,
according to the equation (6):

$$K_{nij} = (I_{nj} - I_{ni})/(j-i) \qquad (6)$$

obtaining the rate of change in pulse intensity $K_{nij}$ over time collected by a single sensor, further, for the peak intensity change, $\Delta IM_{ni-nj}$, the rate of peak signal intensity change is calculated by the equation: $KM_{nij} = \Delta IM_{ni-nj}/(j-i)$.

The above implementations of the invention comprises detecting pulse signal data from pulse sensors, analyzing and displaying pulse data and health information, therefore users can check their physiological conditions conveniently.

The implementation of the invention comprises a device for detection and analysis of health information, characterized in that it comprises:

a first acquisition module for acquiring multiple groups of pulse data detected by a plurality of pulse sensors; and a first analysis module for obtaining physiological characteristics through analysis using calculation methods according to the pulse data;

further, the device for detection and analysis of health information comprises a display control module for sending data to a display screen of a terminal for display.

Figure 2:
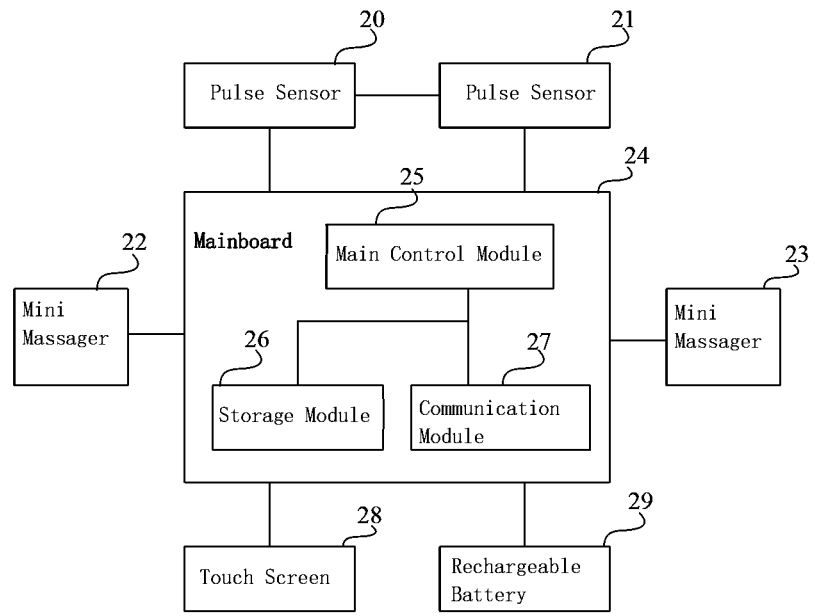
FIG. 2 is a topology map of a device for detection and analysis of health information.

FIG. 2 shows a topology map of the main control module of a detection and analysis device of health information.

It is important to note that this device is one solution associated to the above-described methods, and all implementations of the methods mentioned above are applicable to the embodiments of this device and can also attain the same technical results.

Figure 3:
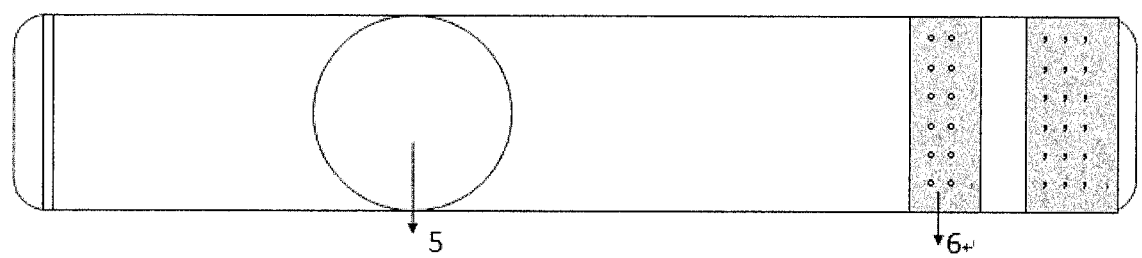
FIG. 3 is an example schematic diagram of a top view of an intelligent health band.

In the implementation of the invention, as shown in FIG. 3, characterized in that it comprises a terminal, and the said terminal comprises the device for detection and analysis of health information, the said device comprises a main control module of the terminal; and the main control module provided on a mainboard of the terminal is electrically connected with two or more than two pulse sensors provided on the terminal.

Further, the mainboard is provided with a storage module and a communication module (such as Bluetooth) which are connected with the main control module.

In some implementations, the said terminal comprises an intelligent health band, or other forms which are equipped with two or more pulse sensors, such as bracelets, watches or mobile phones.

Figure 4:
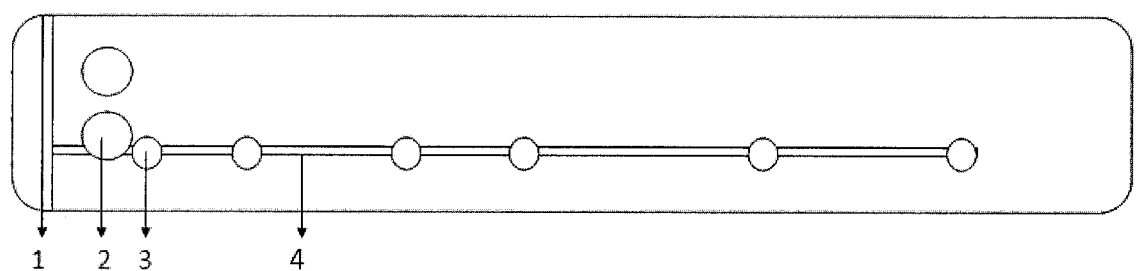
FIG. 4 is an example schematic diagram of a bottom view of an intelligent health band.

In the implementation of a terminal, the terminal comprises an intelligent health band, including a wristband with a touch screen and an electronic module as shown in FIG. 4, and an ankle band with all parts the same as the wristband except the touch screen.

The said electronic control module comprises a main control module as well as a storage module and a Bluetooth module in signal connection with the main control module; and the pulse sensors and the miniature massagers are connected with and controlled by the main control module.

Further, a storage module is equipped for storing detected data; a communication module (such as Bluetooth) is equipped for transmitting detected data and stored data between the band and external equipment, or controlling instructions between the wrist band and the ankle band.

Further, the said main control module is equipped with a timer for timing function.

In some implementations of the device, a rechargeable battery is equipped to power the electronic module.

As shown in FIG. 3 of an example schematic diagram of a top view of an intelligent health band, the band is characterized in that an outer layer of the band is made from a silicone material or a rubber material or a metal material or a bamboo or a wood material or other materials having a width of 0.1-5 cm; the band is provided with Velcro 6 and buckle 1 at both ends to adjust tightness.

In some implementations of the device, the wrist band comprises a touch screen 5 of 0-4 cm in side length, beneath the screen comprises a master control module, a storage module, a communication module (such as Bluetooth), rechargeable battery, etc., and having the cables extending out of both sides of the screen along with the band, connecting with a mini massager 3 and pulse sensors 2, the mini massager 3 is arranged within the sliding groove in the inner side of the band so as to be adjustable in position.

In some implementations of the device, the device comprises a main control module, a storage module, a communication module (such as Bluetooth), rechargeable battery, etc., and connecting with multiple pulse sensors.

In some implementations of the device, the device comprises the pulse sensor which is photoelectrical or piezoelectric or infrared pulse sensor or PPG optical recording apparatus, and two or more than two sensors are mounted linearly at designed positions.

In some implementation of the device as shown in FIG. 4, two pulse sensors 2 are mounted in the inner side of the wristband, therefore, when wearing the wrist band, the pulse sensors 2 are above the radial artery. Further, below the pulse sensors of the inner side of the wristband, a sliding groove 4 is provided along the longitudinal direction of the band, the mini massagers 3 are arranged within the sliding groove 4 so as to be adjustable in one of six positions of acupuncture points (as shown in FIG. 4, six circles on the sliding groove 4).

In some implementations of the device, the structure of the ankle band comprises all the same parts as the wristband except a touch screen. In some other implementations of the device, a touch screen may be installed on the ankle band to fulfill all functions separately in a unit, according to the customer's requirement.

In some implementations of the device, when wearing the wristband, the display screen of the wristband (or a touch screen) is locating at the central part of the back of the wrist, determining the location of the pulse sensors right over the radial artery; and when wearing the ankle band, the main board is locating in the front of the ankle over the dorsal pedal artery.

In some implementations of the device, both the wrist band and the ankle band feature a left-side-wearing type and a right-side-wearing type which are mirror symmetric.

In some implementations of the device, an inner layer of the band is made from a mesh stent rubber material to generate better fitness around the circle of wrist or ankle, improving pulse signal data's accuracy, and providing powerful massage over acupuncture points.

In some implementations of the device, the miniature massager comprises a thin metal post, wherein the area of cross section of the post is in the range of 0-4 $mm^2$, and 0-5 mm in height, the metal post is provided on its end face with three thin cones arranged in the form of a triangle, and rounded dull surfaces are provided on top of the cones.

In some implementations of the device, a mini massager comprises a motor, when the massager is powered on, the motor drives the thin metal post moving up and down in a range of 0-5 mm in height, or rotating circularly at radius of 0-5 mm, to press the corresponding meridian point to play a specific stimulating role.

In some implementations of the device, a mini massager is controlled on a touch screen of the wristband, and the pulse sensors do not work at the same time with the mini massager to ensure the accuracy of collected pulse signal data.

In some implementations of the device, the band is characterized in waterproof and dustproof, and easy to carry and safe to use.

In some implementations of the device, a storage module is for storing monitored data, and a communication module (such as Bluetooth) is for transmitting data between the band and the external devices, and communicating between the wristband and the ankle band for control information.

In the above said implementations of the device, a device comprises: monitoring pulse signal data over the wrist and ankle, and analyzing the multiple groups of pulse signal data for physiological conditions, for user's easy observation of physiological conditions; further, it comprises explaining the health effects of physiological changes based on Chinese and western medicine knowledge; and transmitting stored pulse signal data to the peripheral equipment through Bluetooth or other methods, or presenting individual health information on a touch screen of the wristband, and providing information for medical treatments.

The above described inventive embodiments are the better way of implementing, and illustrated in details herein. Therefore, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. It is understood that the foregoing embodiments are presented by way of example only and that, within the scope of the appended claims and equivalents thereto, inventive embodiments may be practiced otherwise than as specifically described and claimed.

What is claimed is:

1. A method for detection and analysis of health information of a subject with an intelligent health band system comprising a wearable band, wherein the band comprises one or more pulse sensors, one or more massagers, and a mainboard electronically connected to the one or more pulse sensors, the method comprising the steps of:
    (a) acquiring one or more groups of pulse signal data detected by the one or more pulse sensors from the band worn around the subject's wrist or ankle, wherein the step of acquiring the one or more groups of pulse signal data comprises:
    acquiring a group of intensity-time sequence pulse data from each pulse sensor, wherein acquired data from sensor 1, 2, . . . n are expressed as $I1_{i(1,2,3\ldots x)} = I1_1, I1_2, I1_3, \ldots I1_x,$ $I2_{i(1,2,3\ldots x)} = I2_1, I2_2, I2_3, \ldots I2_x,$ and

. . .

$In_{i(1,2,3\ldots x)} = In_1, In_2, In_3, \ldots In_x$ wherein I represents the intensity of pulse signals collected by a pulse sensor, n represents a sensor number and n≥1, and i represents a time sequence number detected, i=1, 2, 3 . . . x, wherein x is the last number of i;
    (b) analyzing the one or more groups of pulse signal data for physiological characteristics by the mainboard, wherein the step of analyzing the one or more groups of pulse signal data comprises:
    obtaining, for each sensor, a difference between effective intensities at an i-th time and a j-th time detected by a n-th sensor according to the following equation:

$\Delta I_{ni-nj} = I_{ni} - I_{nj}$ wherein i and j stand for time sequence number and j>i, and
    wherein when $\Delta I_{ni-nj} - \Delta I_{ni-n(j+1)} \leq 0$, and $\Delta I_{ni-n(j+1)} \leq \Delta I_{ni-n(j+2)}$, and $\Delta I_{ni-n(j-1)} \geq \Delta I_{ni-nj}$, the intensity difference is denoted as $\Delta IM_{ni-nj}$ of the n-th sensor at the j-th time; and,
    obtaining, for each sensor, a series of pulse peak values $IM_{ni}$
    wherein $IM_{ni} = I_{ni}$, when $I_{ni} > I_{n(i+1)}$, and $I_{ni} > I_{n(i-1)}$
        wherein in the series of peak values $IM_{ni}$, a peak distance between in two adjacent peaks $IM_{ni}$ and $IM_{nj}$ is defined as $D_h = (j-i)$, (h=1, 2 . . . ), wherein when $D_h = D_{(h+1)}$, a single pulse duration is $f = (j-i)*a$
    wherein a is a constant of time duration between detected signals, a=1/q and the pulse per minute is 60/f,
    wherein i and j represent different time sequence numbers and j>i, and
    wherein q represents the number of detected signals per second; and
    (c) displaying the physiological characteristics on a display screen on the wearable band.

2. The method for detection and analysis of health information according claim 1, wherein the intelligent health band system further comprises a communication module, and wherein the method further comprises the step of:
    sending, via the communication module, the physiological characteristics to a display screen of a terminal device for display, wherein the terminal device is a bracelet, a watch or a mobile phone.

3. An intelligent health band system, comprising: a wrist band; and an ankle band, wherein each of the wrist band and ankle band comprises one or more pulse sensors, one or more massagers, and a mainboard electronically connected to the one or more pulse sensors, the method comprising the steps of:
    (a) acquiring one or more groups of pulse signal data detected by the one or more pulse sensors from the band worn around the subject's wrist or ankle, wherein the step of acquiring the one or more groups of pulse signal data comprises:
    acquiring a group of intensity-time sequence pulse data from each pulse sensor, wherein acquired data from sensor 1, 2, . . . n are expressed as $I1_{i(1,2,3\ldots x)} = I1_1, I1_2, I1_3, \ldots I1_x,$ $I2_{i(1,2,3\ldots x)} = I2_1, I2_2, I2_3, \ldots I2_x,$ and

. . .

$In_{i(1,2,3\ldots x)} = In_1, In_2, In_3, \ldots In_x$ wherein I represents the intensity of pulse signals collected by a pulse sensor, n represents a sensor number and n≥1, and i represents a time sequence number detected, i=1, 2, 3 . . . x, wherein x is the last number of i;
    (b) analyzing the one or more groups of pulse signal data for physiological characteristics by the mainboard, wherein the step of analyzing the one or more groups of pulse signal data comprises:
    obtaining, for each sensor, a difference between effective intensities at an i-th time and a j-th time detected by a n-th sensor according to the following equation:

$\Delta I_{ni-nj} = I_{ni} - I_{nj}$ wherein i and j stand for time sequence number and j>i, and
    wherein when $\Delta I_{ni-nj} - \Delta I_{ni-n(j+1)} \leq 0$, and $\Delta I_{ni-n(j+1)} \leq \Delta I_{ni-n(j+2)}$, and $\Delta I_{ni-n(j-1)} \geq \Delta I_{ni-nj}$, the intensity difference is denoted as $\Delta IM_{ni-nj}$ of the n-th sensor at the j-th time; and,
    obtaining, for each sensor, a series of pulse peak values $IM_{ni}$
    wherein $IM_{ni} = I_{ni}$, when $I_{ni} > I_{n(i+1)}$, and $I_{ni} > I_{n(i-1)}$
        wherein in the series of peak values $IM_{ni}$, a peak distance between in two adjacent peaks $IM_{ni}$ and $IM_{nj}$ is defined as $D_h = (j-i)$, (h=1, 2 . . . ), wherein when $D_h = D_{(h+1)}$, a single pulse duration is $f = (j-i)*a$
    wherein a is a constant of time duration between detected signals, a=1/q and the pulse per minute is 60/f,
    wherein i and j represent different time sequence numbers and j>i, and
    wherein q represents the number of detected signals per second; and (c) displaying the physiological characteristics on a display screen on the wearable band.

4. The intelligent health band system according to claim 3, wherein the wrist band is provided thereon with a touch control display screen, which is in signal connection with the mainboard in the wrist band, wherein the touch control display screen controls the state of the wrist band and communicates with the ankle band through a communication module wirelessly so as to control the state of the ankle band.

5. The intelligent health band system according to claim 3, wherein the wrist band and/or the ankle band is provided with grooves in its inner side, and the one or more massagers are arranged within the groove so as to be adjustable in position.

6. The intelligent health band system according to claim 3, wherein each of the one or more massagers comprises a motor and a metal post controlled by the motor, wherein the metal post is provided on its end face with three cones arranged in the form of a triangle, and rounded surfaces are provided on top of the cones.

7. The intelligent health band system according to claim 3, wherein each of the one or more pulse sensors is a photoelectrical or piezoelectric or infrared pulse sensor.

8. The intelligent health band system according to claim 3, wherein an outer layer of the wrist and/or ankle band is made from a silicone material or a chemical fiber material having a width of 0.1-5 cm, wherein an inner layer of the wrist and/or ankle band is made from a rubber material, and wherein the wrist and/or ankle band is provided with a hook tape at one end and a loop tape at the other end to adjust tightness.

9. The intelligent health band according to claim 3, wherein both the wrist band and the ankle band feature a left-side-wearing type and a right-side-wearing type which are mirror symmetric.

* * * * *